United States Patent
Hefetz

(10) Patent No.: US 7,671,331 B2
(45) Date of Patent: Mar. 2, 2010

(54) APPARATUS AND METHODS FOR PROCESSING IMAGING DATA FROM MULTIPLE DETECTORS

(75) Inventor: Yaron Hefetz, St. Herzeliya (IL)

(73) Assignee: General Electric Company, Schenectady, NY (US)

(*) Notice: Subject to any disclaimer, the term of this patent is extended or adjusted under 35 U.S.C. 154(b) by 276 days.

(21) Appl. No.: 11/488,402

(22) Filed: Jul. 17, 2006

(65) Prior Publication Data
US 2008/0011954 A1    Jan. 17, 2008

(51) Int. Cl.
*B01D 59/44* (2006.01)
(52) U.S. Cl. ........................................ 250/300
(58) Field of Classification Search ....................... 250/370.01–370.15, 363.01–363.1, 330
See application file for complete search history.

(56) References Cited

U.S. PATENT DOCUMENTS

| | | | |
|---|---|---|---|
| H12 H | 1/1986 | Bennett et al. | |
| 6,140,650 A | 10/2000 | Berlad | |
| 6,239,438 B1* | 5/2001 | Schubert | 250/363.03 |
| 6,748,044 B2* | 6/2004 | Sabol et al. | 378/4 |
| 6,943,355 B2 | 9/2005 | Shwartz et al. | |
| 7,026,623 B2 | 4/2006 | Oaknin et al. | |
| 7,381,959 B2* | 6/2008 | Manjeshwar et al. | 250/363.03 |
| 2002/0191828 A1* | 12/2002 | Colbeth et al. | 382/132 |
| 2005/0145797 A1 | 7/2005 | Oaknin et al. | |
| 2006/0108532 A1 | 5/2006 | Ohana et al. | |
| 2007/0018108 A1* | 1/2007 | Kitamura | 250/363.02 |

FOREIGN PATENT DOCUMENTS

| EP | 1 274 044 A1 | 1/2003 |
|---|---|---|
| WO | WO 9847103 A1 | 10/1998 |
| WO | WO 2004113951 A3 | 12/2004 |

OTHER PUBLICATIONS

Meikle et al., "Accelerated EM reconstruction in total-body PET: potential for improving tumour detectability," 1994, Physics in Medicine and Biology, vol. 39, pp. 1689-1704.*

Riddell et al., "Noise reduction in oncology FDG PET images by iterative reconstruction: a quantitative assessment," 2001, the Journal of Nuclear Medicine, vol. 42, No. 9, pp. 1316-1323.*

Shepp et al., "Maximum likelihood reconstruction for emission tomography," 1982, IEEE Transaction on Medical Imaging, vol. MI-1, No. 2, pp. 113-121.*

* cited by examiner

*Primary Examiner*—David P Porta
*Assistant Examiner*—Kiho Kim
(74) *Attorney, Agent, or Firm*—Dean D. Small; Small Patent Law Group

(57) ABSTRACT

An imaging system comprises a plurality of imaging detectors acquiring imaging data indicative of a patient over a length of time. The plurality of imaging detectors are arranged proximate the patient and remain in a fixed position with respect to the patient. A processor receives the imaging data and divides the imaging data into sub-sets. The processor iteratively processes the sub-sets.

20 Claims, 3 Drawing Sheets

APPARATUS AND METHODS FOR PROCESSING IMAGING DATA FROM MULTIPLE DETECTORS

BACKGROUND OF THE INVENTION

This invention relates generally to Nuclear Medicine imaging systems, and more particularly, to processing data acquired by imaging systems having multiple stationary detectors.

Traditional Nuclear Medicine imaging systems use a small number of large image detectors, such as one, two or three detectors, to acquire imaging data. The image detectors are rotated about a patient to acquire a plurality of projections to create a multi-dimensional image of a structure of interest. For example, 40, 60 or more projections may be acquired. This is very time consuming and requires the patient to lie motionless for an extended period of time. Moreover, the imaging system must comprise a gantry capable of rotating the heavy detectors about the patient.

Using the traditional imaging system, a single detector may be rotated over 180 degrees to acquire 60 projections, each of which is separated by 3 degrees. The detector is positioned at a first position, a first image is acquired, the detector is moved to a second position, a second image is acquired, and so on. Each image produces a 2D representation and has a known symmetry with respect to the other images. Iterative reconstruction algorithms known in the art may then use information about the physical construction and properties of the imaging system to reconstruct the dataset into 3D and/or 4D representations.

Iterative algorithms are computationally intensive and require more computing power and time than what is generally available and acceptable with a current imaging system. Iterative processing takes the full dataset and processes all of the data a number of times, such as twenty times, which is very resource and time intensive. Therefore, techniques such as Ordered Sub-set Expectation Maximization (OSEM) have been developed for accelerating iterative reconstruction algorithms. Ordered Sub-set (OS) methods are based on performing at least the first few iterations (and optionally most or all of the iterations) on a smaller sub-set of the total available dataset. It is important for the conversion of the iterative process that the symmetry of the sub-set be similar to the symmetry of the dataset as a whole.

In the example above, the data may be arranged as a set of angular 2D projections. Using the OS algorithm, the projections within the dataset may be divided into five sub-sets. A first sub-set contains projections 1, 6, 11, . . . , and 56 taken at 3, 18, 33, . . . degrees. A second sub-set contains projections 2, 7, 12, . . . , and 57. Continuing the pattern, a fifth sub-set contains projections 5, 10, 15, . . . , and 60. As each iteration is performed using one sub-set which is a portion of the total dataset, the computation time is shorter.

Imaging systems having multiple smaller-sized detectors are desirable as patient data can be acquired more quickly. The multiple detectors are arranged around a patient and acquire data of the anatomy of interest simultaneously. Unfortunately, the datasets do not have the simple symmetry of projection as discussed above, and thus the algorithms previously used for acceleration of the iterative processing do not apply. Also, the total number of detectors may not produce as rich a dataset as was previously acquired in the 60-90 projections.

Therefore, a need exists for system and methods of iterative processing that may be used with imaging systems acquiring data using multiple stationary detectors. Certain embodiments of the present invention are intended to meet these needs and other objectives that will become apparent from the description and drawings set forth below.

BRIEF DESCRIPTION OF THE INVENTION

In one embodiment, an imaging system comprises a plurality of imaging detectors acquiring imaging data indicative of a patient over a length of time. The plurality of imaging detectors are arranged proximate the patient and remain in a fixed position with respect to the patient. A processor receives the imaging data and divides the imaging data into sub-sets. The processor iteratively processes the sub-sets.

In another embodiment, a method of processing imaging data acquired by a plurality of imaging detectors comprises acquiring imaging data with a plurality of imaging detectors. Each of the plurality of imaging detectors has a plurality of pixels and remains in a fixed position with respect to a patient for an acquisition length of time. The imaging data is divided into sub-sets, and the sub-sets are iteratively processed.

In another embodiment, a method of processing imaging data acquired by a plurality of imaging detectors comprises acquiring imaging data with a plurality of imaging detectors. Each of the plurality of imaging detectors has a plurality of pixels and remains in a fixed position with respect to a patient for an acquisition length of time. The imaging data is divided into sub-sets based on at least one of acquisition time and pixel location. The sub-sets are iteratively processed.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

DETAILED DESCRIPTION OF THE INVENTION

Figure 1:
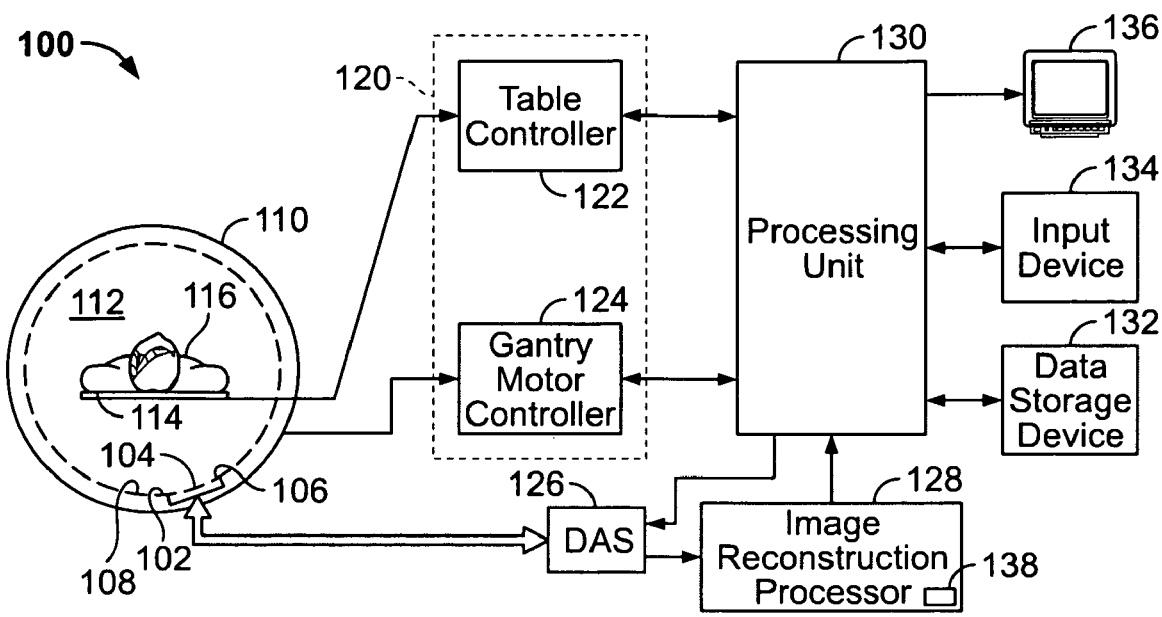
FIG. 1 is a schematic illustration of a Nuclear Medicine (NM) imaging system which has a plurality of small imaging detectors mounted on a gantry formed in accordance with an embodiment of the present invention.

FIG. 1 is a schematic illustration of a Nuclear Medicine (NM) imaging system 100 which has a plurality of small imaging detectors mounted on a gantry. In FIG. 1, first, second, third through N imaging detectors 102, 104, 106 and 108 are mounted on a gantry 110. A conventional imaging detector may be large enough to image most or all of a width of a patient's body at one time and may have a diameter of approximately 40 cm or more. Each of the first, second, third through N imaging detectors 102, 104, 106 and 108 are smaller than a conventional imaging detector. In contrast, each of the first through N imaging detectors 102-108 may have a diameter of 4 cm to 20 cm and may be formed of cadmium zinc telluride (CZT) tiles. The first through N imaging detectors 102-108 may be different sizes and/or shapes with respect to each other, such as square, rectangular, circular or other shape. By positioning multiple imaging detectors at multiple positions with respect to the patient 116, radiation or imaging data specific to a structure of interest within the patient 116 may be acquired without moving the imaging detectors relative to the patient 116.

For example, each of the first through N imaging detectors 102-108 may have 32×32 pixels. Each of the detectors is stationary, viewing the structure of interest from one particular direction. Each detector captures a 2D image which may be defined by the x and y location of the pixel and the detector number.

Each of the first through N imaging detectors 102-108 has a radiation detection face (not shown) which is directed towards a structure of interest within the patient 116. The radiation detection faces are each covered by a collimator (not shown). Different types of collimators may be used, such as pinhole, fan-beam, cone-beam, diverging and parallel-beam type collimators. An actual field of view (FOV) of each of the first through N imaging detectors 102-108 may be directly proportional to the size and shape of the respective imaging detector, or may be changed by using a collimator.

The gantry 110 may have an aperture 112 there-through. A patient table 114 is configured with a support mechanism (not shown) to support and carry the patient 116, optionally, in a plurality of viewing positions within the aperture 112 and relative to the first through N imaging detectors 102-108. Alternatively, the gantry 110 may comprise a plurality of gantry segments (not shown), each of which may independently move one imaging detector or a sub-set of imaging detectors. The gantry 110 may also be configured in other shapes, such as a "C" and "L", for example, and may be rotatable about the patient 116.

In the exemplary imaging system 100, N equals 27, and thus there are 27 imaging detectors arranged in a ring on the gantry 110 around a patient 116. It should be understood that there may be more or less than 27 imaging detectors, and that the imaging detectors may be arranged in an arc, in more than one circle or ring, or other configuration. By way of example, the 27 imaging detectors may be arranged in three C-shaped arches (not shown) of 9 imaging detectors each. Each of the first through N imaging detectors 102-108 is approximately 8×8 cm in size and is equipped with a single pinhole collimator (not shown). The assembly of the first through N imaging detectors 102-108 thus forms an arch of approximately 30 cm of axial width (allowing for gaps between the first through N imaging detectors 102-108 as well as radiation shielding); and spans just over 180 degrees about the patient 116. Optionally, the arch may not be configured as a section of a circle, but instead is constructed to fit to the shape of a typical patient or the particular patient 116. Optionally, the arch is stationary and fixed to a stationary gantry 110. The location of the pinholes of the pinhole collimators relative to the sensitive area of the imaging detector 102-108 may be arranged so that the FOV of all the first through N imaging detectors 102-108 is overlapped on a relatively small volume where the organ to be imaged is located. For example, the organ may be the patient's heart, and the patient 116 is moved to the correct position by moving the patient table 114.

A controller unit 120 may control the movement and positioning of the patient table 114, the gantry 110 and the first through N imaging detectors 102-108 with respect to each other to position the desired anatomy of the patient 116 within the FOVs of the first through N imaging detectors 102-108 prior to acquiring an image of the anatomy of interest. The controller unit 120 may have a table controller 122 and gantry motor controller 124 which may be automatically commanded by a processing unit 130, manually controlled by an operator, or a combination thereof. The gantry motor controller 124 may move the first through N imaging detectors 102-108 with respect to the patient 116 individually in segments or simultaneously in a fixed relationship to one another. The table controller 122 may move the patient table 114 to position the patient 116 relative to the FOV of one or more of the first through N imaging detectors 102-108.

The first through N imaging detectors 102-108, gantry 110, and patient table 114 remain stationary after being initially positioned, and imaging data is acquired and processed as discussed below. The imaging data may be combined and reconstructed into a composite image, which may comprise 2D images, a 3D volume or a 3D volume over time (4D).

A data acquisition system (DAS) 126 receives the electrical signal data produced by the first through N imaging detectors 102-108 and converts the data into digital signals for subsequent processing. An image reconstruction processor 128 and iterative reconstruction module 138 receive data from the DAS 126, and data storage device 132, input device 134, and display 136 may also be provided.

The imaging data from system 100 may be divided according to several methods to achieve symmetry and allow iterative processing. The number of imaging detectors and/or count rate may determine which of the methods is best suited for a particular application and imaging system configuration.

Figure 2:
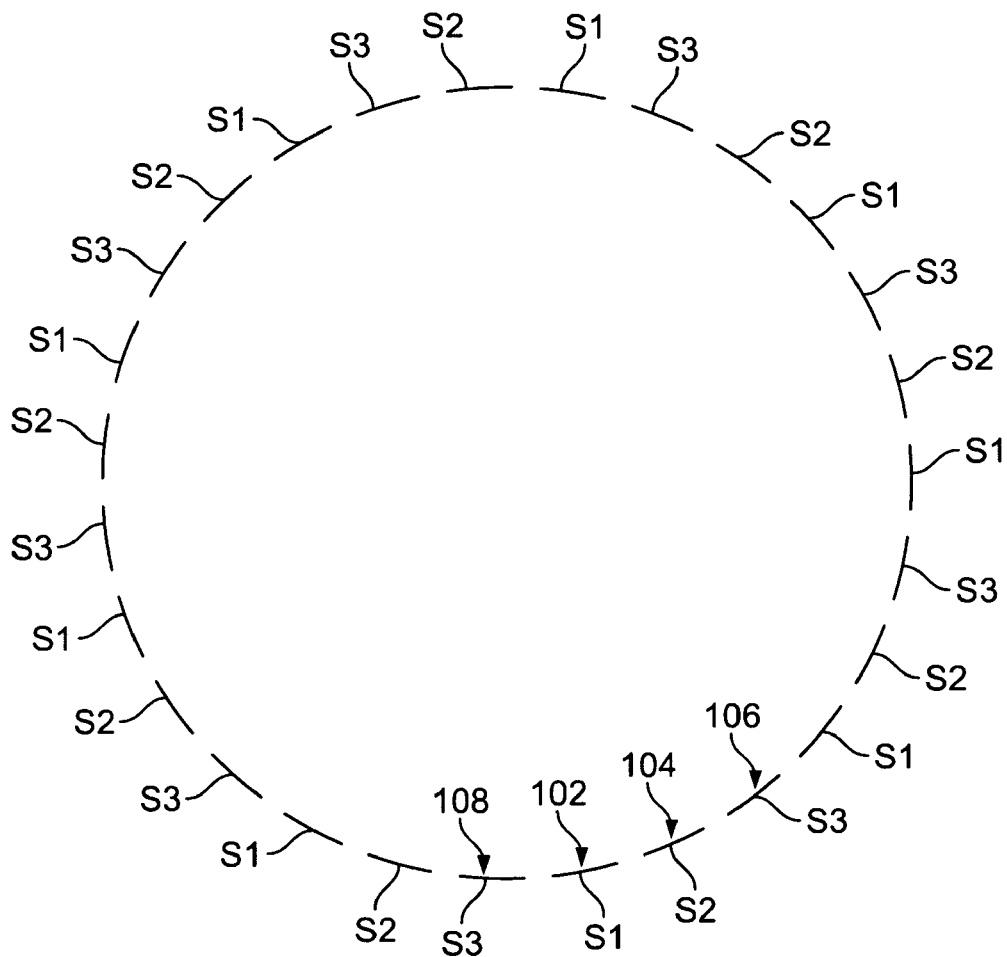
FIG. 2 illustrates an example of dividing the first through N imaging detectors into sub-sets which have the same symmetry as the total dataset in accordance with an embodiment of the present invention.

FIG. 2 illustrates an example of dividing the first through N imaging detectors 102-108 into sub-sets which have the same symmetry as the total dataset. Imaging data is acquired by each of the first through N imaging detectors 102-108. When processing, the iterative reconstruction module 138 assigns data from the first through N imaging detectors 102-108 in an alternate manner to first sub-set (S1), second sub-set (S2) or third sub-set (S3). Therefore, the first, second and third sub-sets each comprise a third of the total dataset, and more or less than three sub-sets may be used. Also, the sub-sets may each comprise the same or a different number of imaging detectors. It may be desirable to have a larger number of imaging detectors wherein at least some of the imaging detectors having partially overlapping FOVs with a neighboring imaging detector to achieve symmetry.

Figure 3:
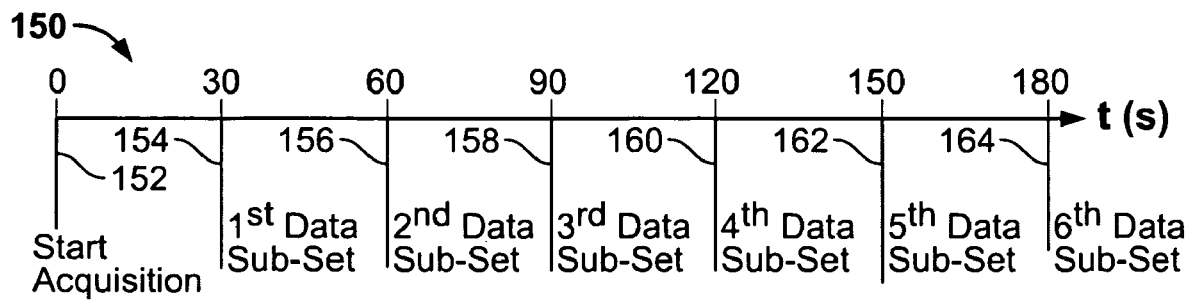
FIG. 3 illustrates an example of dividing the imaging data according to time of acquisition in accordance with an embodiment of the present invention.

FIG. 3 illustrates an example of dividing the imaging data according to time of acquisition. Iterative reconstruction may be performed by the image reconstruction processor 128 and iterative reconstruction module 138 concurrently with data acquisition. This process may be desirable when the count rate is relatively low, creating relatively sparse data-sets wherein some fraction of the pixels do not contain any counts.

Timeline 150 illustrates a total acquisition time of three minutes. The image reconstruction processor 128 processes the imaging data in six sub-sets, and the events may be arranged in a matrix according to their detector and x, y coordinate location. At time equal to 0, the acquisition is started 152. At time equal to 30 seconds, the iterative reconstruction module 138 requests that the DAS 126 send first data sub-set 154 comprising event data acquired during the acquisition time from 0-29 seconds from the first through N imaging detectors 102-108. The image reconstruction processor 128 begins to process the first data sub-set 154 while the first through N imaging detectors 102-108 continue to acquire imaging data.

At time equal to 60 seconds, the iterative reconstruction module 138 requests the DAS 126 send second data sub-set 156 comprising event data acquired during the acquisition time from 30-59 seconds from the first through N imaging detectors 102-108. The image reconstruction processor 128 begins to process the second data sub-set 156 concurrently with processing the first data sub-set 154, and the first through N imaging detectors 102-108 continue to acquire data. This process repeats for the time duration of the acquisition, acquiring third data sub-set 158, fourth data sub-set 160, fifth data sub-set 162 and sixth data sub-set 164.

Alternatively, as the events are acquired, the events may be registered as "list-mode", or listed in a list-mode file according to time of arrival or detection. In this example, each of the first through N imaging detectors 102-108 sends event data to the DAS 126 as each event is acquired. Each of the events is identified by the imaging detector number and x, y coordinate location. At time equal to 30 seconds, the iterative reconstruction module 138 may request the DAS 126 to send first data sub-set 154 which comprises a first list of all acquired events from each of the first through N imaging detectors 102-108. There is no need for the image reconstruction processor 128 to visit pixels which are empty or did not count an event. The image reconstruction processor 128 begins to process the first data sub-set 154 concurrently with the DAS 126 building a subsequent list of the next sub-set of data. At time equal to 60 seconds, the iterative reconstruction module 138 requests the DAS 126 to send the second data sub-set 156 comprising the second list of acquired events. The image reconstruction processor 128 begins to process the second data sub-set 156 concurrently with processing the first data sub-set 154, while the DAS 126 builds a next list for the next sub-set of data. The process is repeated until the acquisition is complete.

Additionally, a list-mode file may store data essentially in order of detection time. The stored file may include other data such as actual time, physiological patient information such as ECG readings, and information about procedures relative to the patient, such as time of injection of radioactive isotope and the like. The processing of list-mode data may be done concurrently with the acquisition, or the list-mode file may be stored and processed at a later time. Additionally, the list-mode file may be processed in different ways at later times. For example, the list-mode file may be divided into a different number of time sub-sets of data.

Figure 4:
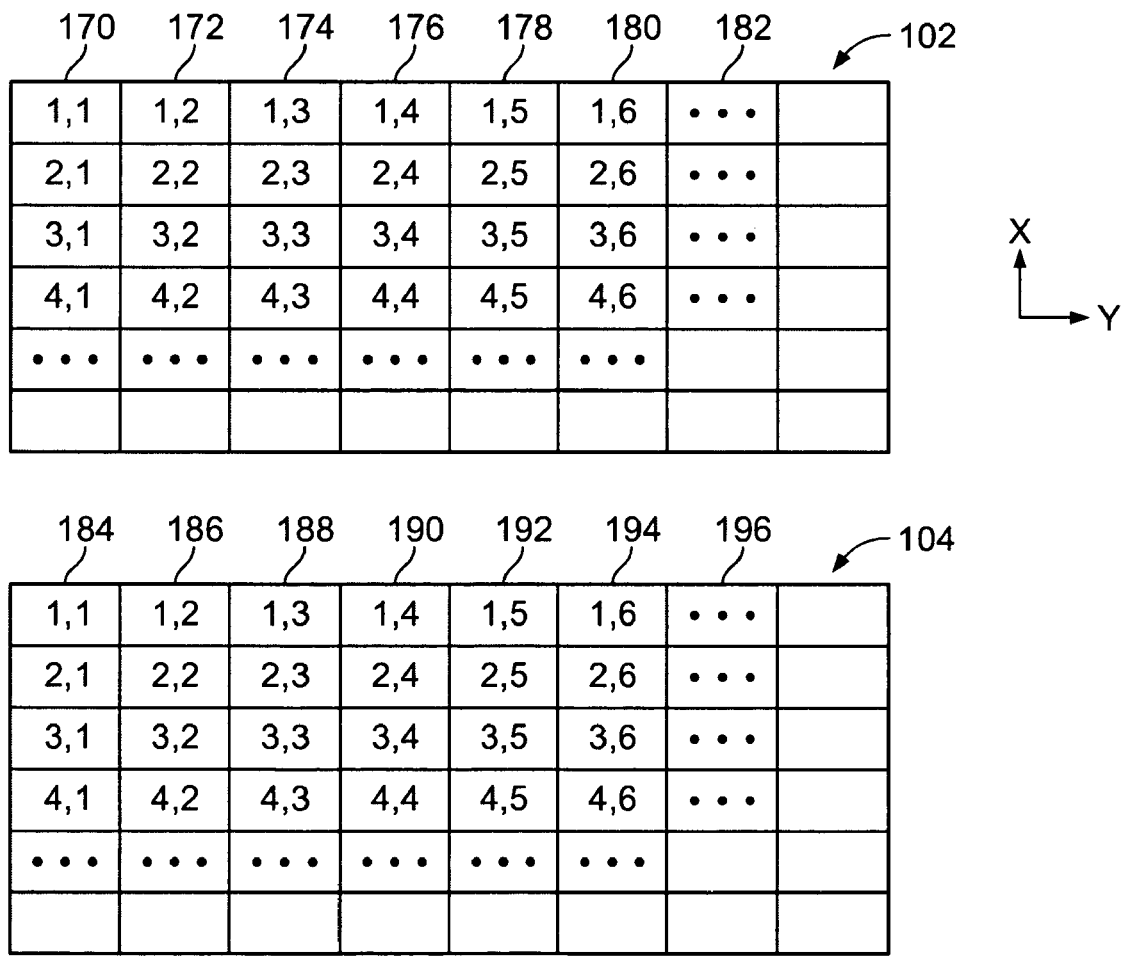
FIG. 4 illustrates an example of forming sub-sets by assigning pixels to different sub-sets in accordance with an embodiment of the present invention.

FIG. 4 illustrates an example of forming sub-sets by assigning pixels to different sub-sets. For example, sub-set k contains pixels with designation: {Detector #=D, X coordinate=N*S+k, coordinate=Y); where: D={1, 2, ... d}, d is the number of detectors, k is the sub-set number, s is the number of sub-sets, N={12, ... , x/s}, x is the number of pixels in a row, Y={12, ... , y}, and y is the number of pixels in a column.

First and second imaging detectors 102 and 104 are illustrated, each having a matrix of pixels. Each pixel has an x, y coordinate. Three sub-sets of data are formed by dividing the pixels based on columns. First columns 170 and 184, fourth columns 176 and 190, seventh columns 182 and 196, and so on of the first and second imaging detectors 102 and 104, respectively, form the first sub-set. Second columns 172 and 186, fifth columns 178 and 192, and eighth columns (not shown) and so on form the second sub-set, and third columns 174 and 188, sixth columns 180 and 194, and ninth columns (not shown) form the third sub-set. The process may be repeated for the remaining third through N imaging detectors 106-108.

Figure 5:
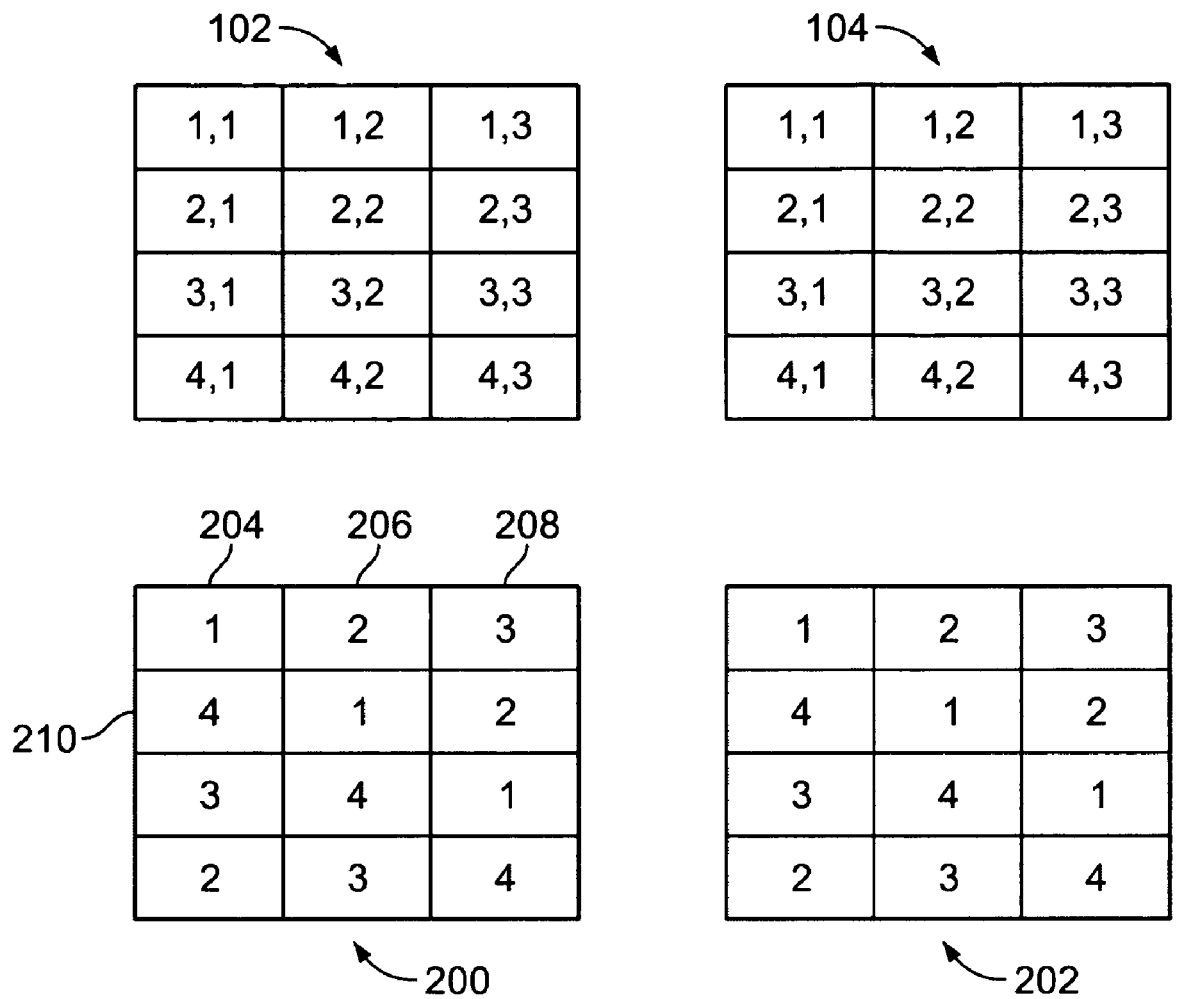
FIG. 5 illustrates an alternative method for assigning pixels of imaging detectors to different sub-sets in accordance with an embodiment of the present invention.

FIG. 5 illustrates an alternative method for assigning pixels of imaging detectors to different sub-sets. Using the parameters defined in FIG. 4, FIG. 5 illustrates forming sub-sets using k=Mode [(X+Y*x), s]. Detector coordinates of pixels are alternatively assigned to one of four sub-sets. Therefore, each sub-set will have one-fourth of the total imaging data. First and second imaging detectors 102 and 104 are again illustrated with a matrix of pixels. First and second matrixes 200 and 202 illustrate assignments of coordinates of the first and second imaging detectors 102 and 104, respectively. First coordinate location 204 is indicated as "1" and detected photons are assigned to a first sub-set. Second coordinate location 206 is indicated as "2" and detected photons are assigned to a second sub-set. Third and fourth coordinate locations 208 and 210 are indicated with "3" and "4", respectively, and detected photons are assigned to third and fourth sub-sets. Each data sub-set forms a low resolution image representative of data acquired by the entire respective imaging detector.

Alternatively, the detector coordinates may be assigned to three sub-sets in a similar manner as discussed above. If two sub-sets are desired, the detector coordinates may be assigned based on a checkerboard pattern. Alternatively, the pixel locations may be assigned to one of N sub-sets randomly or pseudo-randomly, or based on any other pattern, such as based on anatomy being imaged.

Techniques may be combined, such as dividing data both by time and by detector coordinates. For example, a patient study may be set to acquire data for six minutes. At three minutes, the iterative reconstruction module 138 may request the data collected during the first three minutes of the acquisition by the first through N imaging detectors 102-108. The iterative reconstruction module 138 may then divide the data into three sub-sets based on column or row location, as illustrated in FIG. 4. Processing may then be performed on the three sub-sets, and alternatively also on the sub-set comprising all of the data acquired during the first three minutes, concurrently with acquiring the second three minutes of data. The second three minutes of data may be divided and processed in the same manner. The total data is thus divided into 6 smaller sub-sets, and the computation time is approximately one-sixth of the time required for a full computation.

Figure 6:
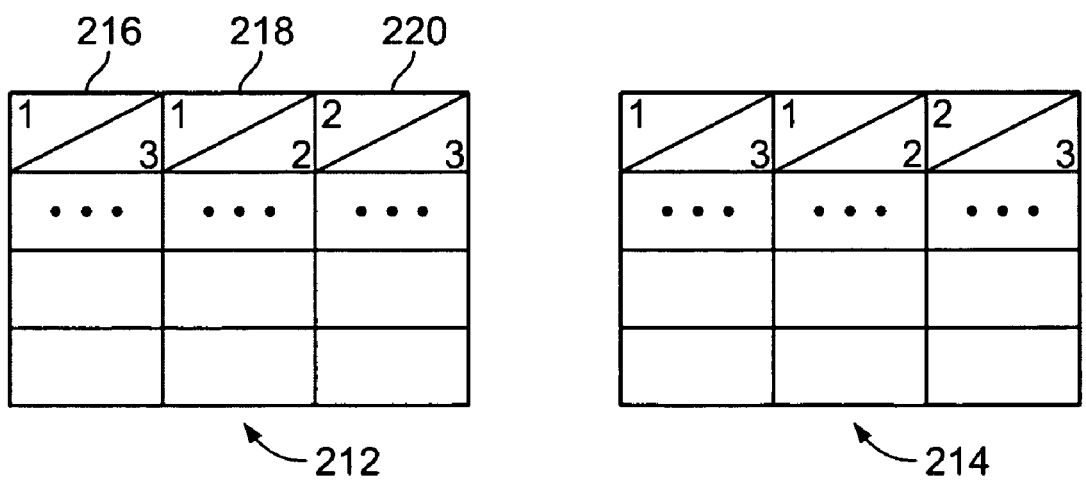
FIG. 6 illustrates first and second coordinate matrixes corresponding to the first and second imaging detectors, respectively, of FIG. 5 in accordance with an embodiment of the present invention.

The data does not need to be divided into groups which are foreign or separate with respect to each other. The data may be over-sampled by dividing the data into overlapping sub-sets. FIG. 6 illustrates first and second coordinate matrixes 212 and 214 corresponding to the first and second imaging detectors 102 and 104, respectively, of FIG. 5. Three sub-sets are used, and each coordinate location is included in two of the sub-sets. First coordinate location 216 is included in both first and third sub-sets, second coordinate location 218 is included in both first and second sub-sets, and third coordinate location 220 is included in both second and third sub-sets. The sub-sets may overlap in one or both of time and geometry.

The data may also be divided into unequal sub-sets over time, creating a sub-set of data acquired over a longer period of time (thus having a greater amount of data and being more "rich") towards the end of the iteration process. Alternatively, the sub-sets iteratively processed in the later part of the process may be larger or may comprise the full dataset.

The processing time may be further decreased by using a parallel computing device such as an array processor or graphic accelerator. Also, multiple processors may be included in the image reconstruction processor 128, iterative reconstruction module 138, and processing unit 130. Optionally, a plurality of computers or processors may be used in any configuration, such as sending one or more sub-sets of data over a data link such as the internet to a remote computer for iterative processing. The remote computer then may return the processed data to the host system.

A technical effect is efficiently processing imaging data acquired with a plurality of imaging detectors which are small in size and held stationary during the acquisition. The imaging data may be divided into sub-sets of data and processed separately from one another. The processing time is reduced, as is the time needed to acquire the patient study. One or more sub-sets of data may be processed concurrently while the imaging detectors continue to acquire imaging data. The sub-sets may be divided based on time, geometry, or both. The sub-sets may be equal or different in size, separate, overlapping, assigned randomly, and/or generated based on one or more pattern.

While the invention has been described in terms of various specific embodiments, those skilled in the art will recognize that the invention can be practiced with modification within the spirit and scope of the claims.

What is claimed is:

1. An imaging system, comprising:
a first and a second set of imaging detectors acquiring imaging data indicative of a patient over a length of time, the plurality of imaging detectors being arranged proximate the patient and remaining in a fixed position with respect to the patient, wherein the first set of imaging detectors are interleaved with the second set of imaging detectors; and
a processor receiving the imaging data, the processor assigning the imaging data into subsets based on at least one of a detector number and a pixel location, the processor iteratively processing the sub-sets, wherein iteratively processing the sub-sets comprises iteratively reconstructing at least one of the sub-sets.

2. The system of claim 1, wherein each of the plurality of imaging detectors further comprises a plurality of pixels arranged in rows and columns, the processor further assigning one of a first row and a first column to a first sub-set and one of a second row and a second column to a second sub-set.

3. The system of claim 1, wherein each of the plurality of imaging detectors further comprises a plurality of pixels arranged in rows and columns, the processor assigning the imaging data into at least two sub-sets based on one of at least an alternating row pattern, an alternating column pattern, a checkerboard pattern, a random assignment, and a pseudo-random assignment.

4. The system of claim 1, wherein a first subset of the imaging data is acquired from the first set of imaging detectors and a second subset of the imaging data is acquired from the second set of imaging detectors.

5. The system of claim 4, wherein the imaging detectors in the first set are separated from one another by the imaging detectors in the second set.

6. The system of claim 1, wherein a first subset includes imaging data acquired from a first set of imaging detectors that are equidistantly spaced from one another around the patient and a second subset includes imaging data acquired from a different second set of imaging detectors that are equidistantly spaced from one another around the patient.

7. The system of claim 1, wherein the processor assigns the imaging data into N subsets each subset including 1/N of the imaging data.

8. The system of claim 1, wherein the processor assigns the imaging data in an alternating pattern into subsets based on the detector number.

9. The system of claim 1, wherein the processor assigns the imaging data in an alternating pattern into subsets based on the pixel location.

10. A method of processing imaging data acquired by a plurality of imaging detectors, comprising:
acquiring imaging data with a plurality of imaging detectors, each of the plurality of imaging detectors remaining in a fixed position with respect to a patient for an acquisition length of time, each of the plurality of imaging detectors having a plurality of pixels;
assigning the imaging data in an alternating pattern into sub-sets based on an imaging detector number; and
iteratively processing the sub-sets including iteratively reconstructing at least one of the sub-sets.

11. The method of claim 10, wherein the plurality of pixels are arranged in rows and columns, the method further comprising assigning one of a first row and a first column to a first sub-set and one of a second row and a second column to a second sub-set.

12. The method of claim 10, wherein the plurality of pixels are arranged in rows and columns, the method further comprising assigning the imaging data into at least two sub-sets based on one of an alternating row pattern and an alternating column pattern.

13. The method of claim 10, wherein the plurality of pixels are arranged in rows and columns, the method further comprising assigning the imaging data based on at least one of a checkerboard pattern, a random assignment, and a pseudo-random assignment.

14. The method of claim 10, further comprising:
acquiring the imaging data in list-mode; and
defining first and second sub-sets comprising first and second list-mode files, the second sub-set being acquired subsequent to the first sub-set.

15. The method of claim 10, wherein each of the plurality of pixels has a pixel location, the sub-sets further comprising at least first and second sub-sets, the first and second sub-sets at least partially overlapping each other with respect to at least one of the pixel location and acquisition time period.

16. A method of processing imaging data acquired by a plurality of imaging detectors, comprising:
acquiring imaging data with a plurality of imaging detectors, each of the plurality of imaging detectors remaining in a fixed position with respect to a patient for an acquisition length of time, each of the plurality of imaging detectors having a plurality of pixels;
assigning the imaging data in an alternating pattern into sub-sets based on a pixel location; and
iteratively processing the sub-sets sets including iteratively reconstructing at least one of the sub-sets.

17. The method of claim 16, the iteratively processing further comprising processing the imaging data from each of the plurality of imaging detectors for N iterations, at least one of the iterations being performed on a sub-set comprising a full dataset of imaging data.

18. The method of claim 16, wherein the sub-sets are one of a same size and a different size with respect to each other.

19. The method of claim 16, wherein at least a portion of the sub-sets comprise at least a portion of the same imaging data.

20. The method of claim 16, the iteratively processing further comprising parallel processing the sub-sets of imaging data.

* * * * *